US011630095B2

United States Patent
Borrowman et al.

(10) Patent No.: US 11,630,095 B2
(45) Date of Patent: Apr. 18, 2023

(54) X-RAY SEED IMAGING SYSTEM, CABINET X-RAY DEVICE, AND METHODS OF EVALUATING SEEDS

(71) Applicant: Monsanto Technology LLC, St. Louis, MO (US)

(72) Inventors: Eric Borrowman, St. Louis, MO (US); Donald J. Essner, St. Louis, MO (US); Alfred B. Garson, III, St. Louis, MO (US); Govind Chaudhary, St. Louis, MO (US); Johnny J. Kotyk, Manchester, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 50 days.

(21) Appl. No.: 17/096,405

(22) Filed: Nov. 12, 2020

(65) Prior Publication Data
US 2021/0140900 A1    May 13, 2021

Related U.S. Application Data

(60) Provisional application No. 62/934,855, filed on Nov. 13, 2019.

(51) Int. Cl.
*G01N 33/00* (2006.01)
*G01N 23/04* (2018.01)
*G01N 23/083* (2018.01)

(52) U.S. Cl.
CPC ......... *G01N 33/0098* (2013.01); *G01N 23/04* (2013.01); *G01N 23/083* (2013.01);
(Continued)

(58) Field of Classification Search
None
See application file for complete search history.

(56) References Cited

U.S. PATENT DOCUMENTS

| 2,849,619 A | * | 8/1958 | Eisfeldt | H01J 37/20 250/442.11 |
| 3,177,360 A | * | 4/1965 | Hague, Jr. | G01N 23/20025 378/81 |

(Continued)

FOREIGN PATENT DOCUMENTS

| CN | 103347381 B | * | 12/2015 | ............... G01N 1/08 |
| CN | 106650802 A | * | 5/2017 | ............. G01N 23/04 |

(Continued)

OTHER PUBLICATIONS

International Search Report and Written Opinion for PCT/US20/60242, dated Feb. 5, 2021, 10 pages.
(Continued)

*Primary Examiner* — Thomas R Artman
(74) *Attorney, Agent, or Firm* — Harness, Dickey & Pierce, P.L.C.

(57) ABSTRACT

A cabinet x-ray device for imaging seeds includes an x-ray source configured to transmit an x-ray beam along a beam path. A seed holder is configured to hold seeds and be selectively positioned in the x-ray device such that the beam path crosses the seed holder and the x-ray beam passes through at least some of the seeds. An x-ray detector is configured to detect the x-ray beam after passing through the seeds such that one or more x-ray images of the seeds can be formed. Self-supporting x-ray shielding can extend circumferentially around the x-ray beam to mitigate x-ray transmission outside the device. A drive mechanism can automatically move the seed holder so that discrete x-ray images of subsets of seeds are taken in an automatic seed imaging operation. Various seed evaluations and seed process evaluations can be made using the device.

21 Claims, 10 Drawing Sheets

(52) U.S. Cl.
CPC . *G01N 2223/04* (2013.01); *G01N 2223/1016* (2013.01); *G01N 2223/301* (2013.01); *G01N 2223/307* (2013.01); *G01N 2223/308* (2013.01); *G01N 2223/3306* (2013.01); *G01N 2223/40* (2013.01); *G01N 2223/612* (2013.01); *G01N 2223/64* (2013.01)

(56) References Cited

U.S. PATENT DOCUMENTS

| | | | | |
|---|---|---|---|---|
| 3,488,495 | A * | 1/1970 | Schneeman | G21F 7/047 250/493.1 |
| 4,357,535 | A | 11/1982 | Haas | |
| 4,809,308 | A * | 2/1989 | Adams | G01N 23/18 378/98.2 |
| 5,113,425 | A * | 5/1992 | Zweig | G01N 23/043 378/57 |
| RE35,423 | E * | 1/1997 | Adams | G01R 31/304 378/98.2 |
| 7,082,185 | B2 * | 7/2006 | Freifeld | G01N 23/04 378/53 |
| 7,105,813 | B2 * | 9/2006 | Lee | H01J 49/04 250/306 |
| 7,529,338 | B2 * | 5/2009 | Fung | G01N 23/043 378/208 |
| 7,742,564 | B2 * | 6/2010 | Parham | G01N 23/046 378/85 |
| 8,189,901 | B2 * | 5/2012 | Modiano | B07C 5/34 47/14 |
| 9,188,553 | B2 * | 11/2015 | Sakuta | G01N 23/223 |
| 9,492,130 | B2 * | 11/2016 | Flagle | A61B 6/4405 |
| 9,865,424 | B2 * | 1/2018 | Ikeda | G01V 5/0016 |
| 10,078,093 | B2 * | 9/2018 | Flagle | G01N 35/04 |
| 10,557,805 | B2 * | 2/2020 | Chaudhary | G01N 23/046 |
| 10,830,711 | B2 * | 11/2020 | Kondo | H05G 1/025 |
| 11,020,066 | B2 * | 6/2021 | Butani | A61B 6/4208 |
| 11,044,843 | B2 * | 6/2021 | Kotyk | B07C 5/3425 |
| 11,083,426 | B2 * | 8/2021 | Defreitas | G01N 23/04 |
| 2004/0218716 | A1 | 11/2004 | Freifeld et al. | |
| 2005/0056777 | A1 * | 3/2005 | Lee | H01J 49/04 250/281 |
| 2007/0291896 | A1 | 12/2007 | Parham et al. | |
| 2008/0310674 | A1 | 12/2008 | Modiano et al. | |
| 2013/0176553 | A1 * | 7/2013 | Cope | G01N 21/314 356/402 |
| 2013/0229647 | A1 | 9/2013 | Fredlund et al. | |
| 2013/0231585 | A1 * | 9/2013 | Flagle | G01N 35/04 600/565 |
| 2014/0257135 | A1 | 9/2014 | DeFreitas et al. | |
| 2014/0286474 | A1 * | 9/2014 | Sakuta | G01N 23/223 378/44 |
| 2015/0135585 | A1 * | 5/2015 | Cope | B01L 3/50 47/14 |
| 2015/0179391 | A1 * | 6/2015 | Ikeda | H05G 1/025 378/68 |
| 2015/0321353 | A1 | 11/2015 | McCarty, II et al. | |
| 2017/0131311 | A1 * | 5/2017 | Flagle | A61B 10/0283 |
| 2017/0295735 | A1 | 10/2017 | Butruille et al. | |
| 2018/0217072 | A1 | 8/2018 | Chaudhary et al. | |
| 2019/0281781 | A1 | 9/2019 | Borrowman et al. | |
| 2019/0285558 | A1 | 9/2019 | DeFreitas et al. | |
| 2019/0307055 | A1 | 10/2019 | Kotyk et al. | |
| 2019/0346471 | A1 * | 11/2019 | Flagle | G01N 35/04 |
| 2020/0182807 | A1 * | 6/2020 | Butani | G01N 23/20025 |
| 2021/0140900 | A1 * | 5/2021 | Borrowman | G01N 23/04 |
| 2022/0039766 | A1 * | 2/2022 | Defreitas | A61B 6/4452 |

FOREIGN PATENT DOCUMENTS

| | | | | |
|---|---|---|---|---|
| CN | 107238620 | A * | 10/2017 | G01N 23/2204 |
| CN | 106650802 | B * | 7/2019 | G01N 23/04 |
| FR | 2549963 | A1 * | 2/1985 | G01N 23/12 |

OTHER PUBLICATIONS

S. K. Kamra, The X-ray Contrast Method for Testing Germinability of *Picea abies* (L.) Karst. seed, Studia Forestalia Suecica Nr. 90, 1971, 28 pages, Skogshogskolan, Royal College of Forestry, Stockholm.

* cited by examiner

X-RAY SEED IMAGING SYSTEM, CABINET X-RAY DEVICE, AND METHODS OF EVALUATING SEEDS

FIELD

The present disclosure generally relates to an x-ray seed imaging system, a cabinet x-ray device, and methods for evaluating seeds using a cabinet x-ray device.

BACKGROUND

In the agricultural industry, and more specifically in the seed breeding and production industry, scientists seek ways to analyze seeds that undergo processing. Typically seed processes are carried out at production facilities remote from agricultural facilities where seeds are grown and initially held. Further, seed processes involve multiple processing steps that can be conducted on separate equipment at separate locations. It may be desirable to analyze seeds before transporting them to the production facility and/or at any step in a production process.

One method for analyzing seeds involves taking x-ray images of the seeds and then evaluating the appearance of the seeds in the x-ray images. Typical x-ray equipment for making this type of analysis is very large and/or requires dedicated infrastructure for operation. This can limit the use of x-ray imaging to analyze seeds at sites that are remote from where x-ray equipment is installed.

SUMMARY

In one aspect, a cabinet x-ray device for imaging seeds comprises an x-ray source configured to transmit an x-ray beam along a beam path. A seed holder is configured to receive a plurality of seeds and be selectively positioned in the cabinet x-ray device such that the beam path crosses the seed holder and the x-ray beam passes through at least some of the seeds received in the seed holder. An x-ray detector is configured to detect the x-ray beam after passing through the seeds such that one or more x-ray images of the seeds can be formed based on the detected x-ray beam.

In another aspect, a cabinet x-ray device comprises an x-ray source configured to transmit an x-ray beam along a beam path. The x-ray source has a weight. An x-ray detector is configured to detect the x-ray beam. The x-ray detector has a weight. X-ray shielding extends circumferentially around the beam path from the x-ray source to the x-ray detector. The x-ray shielding is configured to limit transmission of x-rays from the x-ray beam outside of the x-ray shielding. At least one of the x-ray source and the x-ray detector is mounted on the x-ray shielding such that the weight of said at least one of the x-ray source and the x-ray detector is supported on the shielding.

In still another aspect, a method of analyzing seeds comprises transporting a cabinet x-ray device to a first location where seeds are held prior to being transported to a production facility at a second location remote from the first location. X-ray images of a set of the seeds are taken at the first location. An evaluation of the seeds in the set is made based on the x-ray images taken using the cabinet x-ray device.

In yet another aspect, a method of evaluating a seed process having a plurality of process steps carried out at discrete locations comprises transporting a cabinet x-ray device to each of the discrete locations. For each process step, a set of seeds is collected that have been processed at that process step and one or more x-ray images of the collected set of seeds are taken using the cabinet x-ray device at the respective discrete location. Each of the plurality of process steps is evaluated based on the x-ray images.

In another aspect, a method of evaluating seeds comprises placing a set of seeds into each of a plurality of sample wells in a seed holder. The seed holder is positioned in a cabinet x-ray device at a plurality of spaced apart predefined positions. An x-ray beam of the cabinet x-ray intersects each of the sample wells at a respective one of the plurality of predefined positions of the seed holder. An x-ray image of a respective set of seeds is taken using the cabinet x-ray device when the seed holder is positioned at each of the predefined positions.

Other aspects will be in part apparent and in part pointed out hereinafter.

BRIEF DESCRIPTION OF THE DRAWINGS

Corresponding reference numbers indicate corresponding elements throughout the drawings.

DETAILED DESCRIPTION

Figure 1:
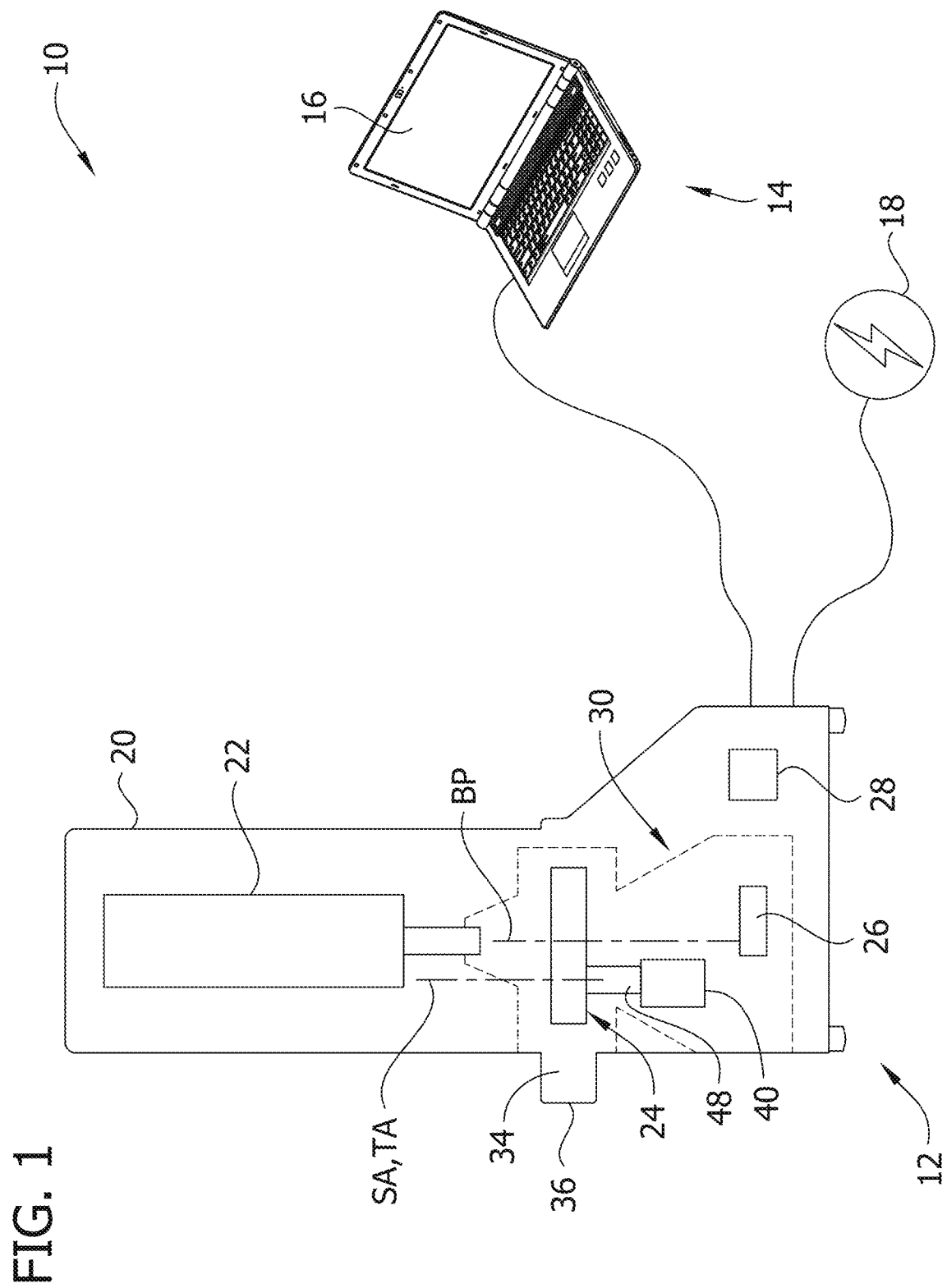
FIG. 1 is a schematic illustration of an x-ray seed imaging system.

Referring to FIG. 1, an exemplary embodiment of an x-ray seed imaging system is generally indicated at reference number 10. The seed imaging system 10 broadly includes an x-ray device, generally indicated at 12, and a computer, generally indicated at 14. The x-ray device 12 is configured to take x-ray images of seeds (or other types of specimen), and the computer 14 is configured to display the x-ray images on a display 16 and/or analyze the x-ray images to identify one or more parameters of the seeds. Suitable computer-implemented methods for analyzing x-ray images of seeds are disclosed in U.S. patent application Ser. No. 16/271,005, which is hereby incorporated by reference in its entirety.

The seed imaging system 10 is configured to be relatively portable so that x-ray images of seeds can be taken and/or analyzed at various locations, including sites upstream of seed manufacturing facilities in seed process, e.g., an agricultural field or farm where seeds are grown or initially stored. Thus, in one or more embodiments, the computer 16 comprises a portable computer such as a laptop computer, a tablet computer, or a mobile phone. In addition, the x-ray device 12 is relatively lightweight and has relatively small external dimensions. For example, in the illustrated embodiment, the x-ray device weighs less than 50 pounds (e.g., 35 pounds or less) and fits inside an imaginary hexahedron with dimensions of 36 inches by 24 inches by 24 inches (e.g., an imaginary hexahedron having a height that is less than 30 inches and a length and a width that are each less than 12 inches). This allows a single person to carry the device 12 and facilitates transportation of the device in the bed of a standard pickup truck (or other passenger vehicle cargo area). To further enhance portability, the illustrated x-ray device 12 is configured to be selectively powered by both a 110-volt alternating current source and a 12-volt direct current battery. Thus, to power the device 12 during operation, a user can simply plug it into a standard wall socket or, for example, a seven-pin trailer light outlet on a motor vehicle that is connected to a vehicle battery.

Figure 2:
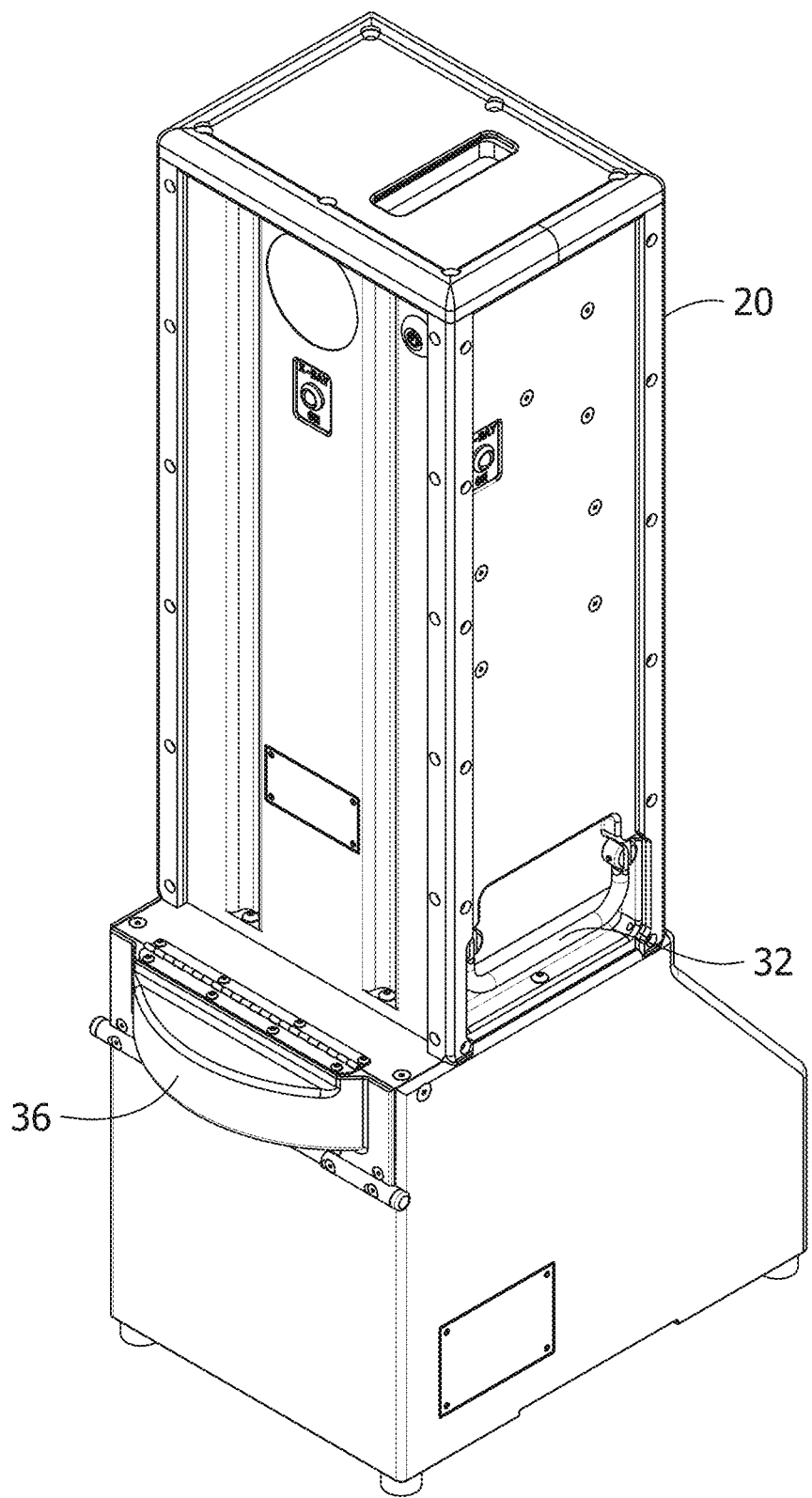
FIG. 2 is a perspective of a cabinet x-ray device of the x-ray seed imaging system.
Figure 3:
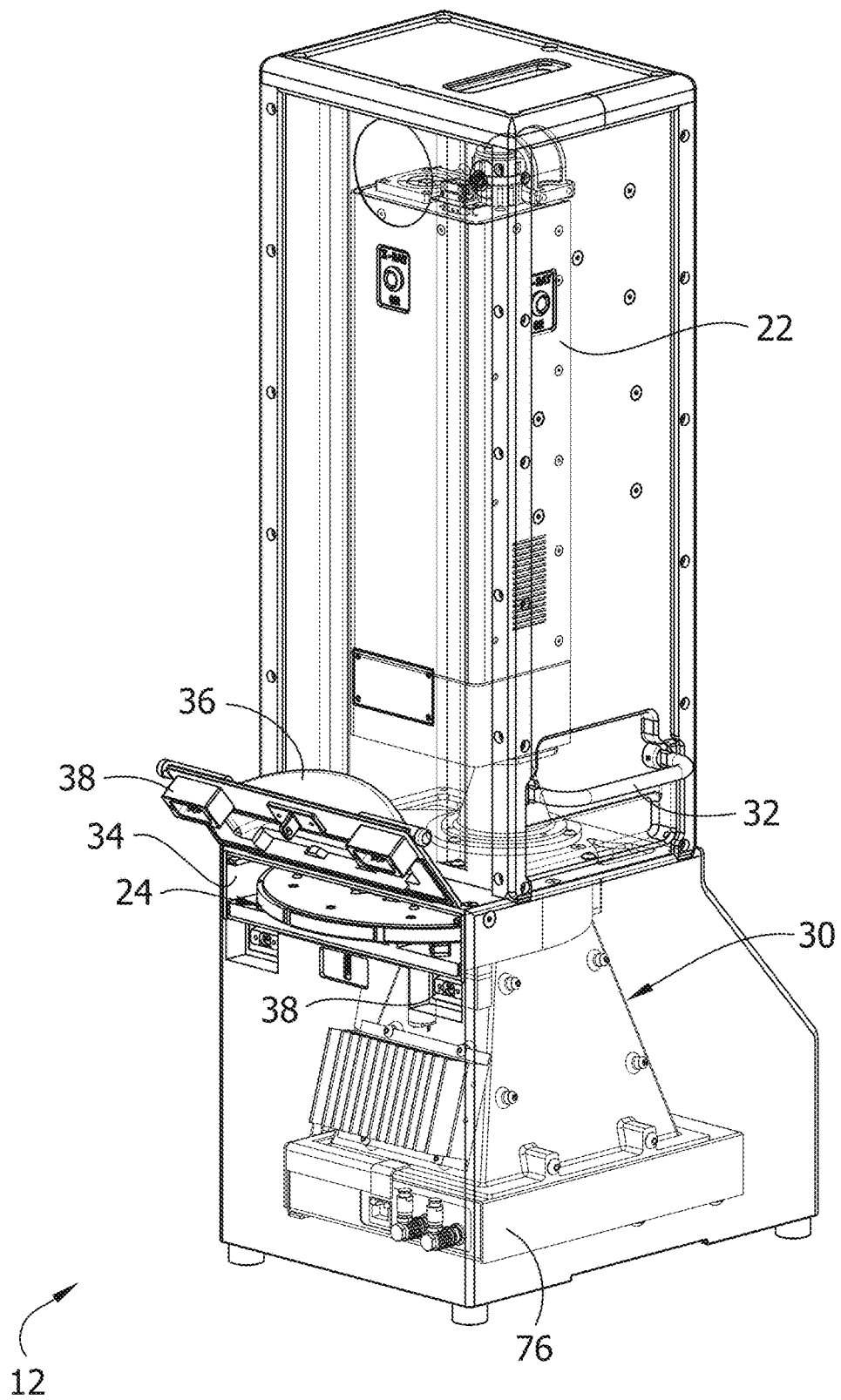
FIG. 3 is a perspective similar to FIG. 2, in which a cabinet of the cabinet x-ray device is depicted to be transparent and a door of the cabinet x-ray device is shown in an open position.

Referring to FIGS. 1-3, the illustrated x-ray device 12 is of the type commonly referred to as a cabinet x-ray device. As such, the x-ray device 12 comprises a cabinet 20 that is configured to fully enclose the x-ray systems during operation. The illustrated cabinet houses an x-ray source 22 configured to transmit an x-ray beam along a beam path BP (FIG. 1) that intersects a specimen holder 24. An x-ray detector 26 is configured to detect the x-ray beam after passing through a specimen received in the holder 24. The aspect of the x-ray beam that is detected by the detector 26 may be referred to as the "shadow" of the x-ray beam. X-ray shielding, generally indicated at 30, extends circumferentially around the beam path BP from the x-ray source 22 to the x-ray detector 26 and limits transmission of x-rays from the x-ray beam outside of the x-ray shielding. For example, in one or more embodiments, the x-ray shielding is configured to comply with the regulations of the United States Food and Drug Administration regarding maximum radiation emission of cabinet x-ray systems set forth in Title 21 of the Code of Federal Regulations.

The cabinet 20 functions as an external enclosure around the x-ray systems of the device 12. In one or more embodiments, the cabinet 20 can be made weather-tight. As explained above, the x-ray device is relatively light weight and has relatively small external dimensions. Thus, in the illustrated embodiment, the cabinet comprises handles 32 for use in carrying the device 12. The cabinet 20 also defines a doorway 34 through which the holder 24 (or, more broadly, a specimen such as a set of seeds) is passable into and out of the cabinet. A door 36 is movably connected to the cabinet 20 (e.g., by a hinge) for selective movement between a closed position at which the door closes the doorway 34 and an open position at which the door opens the doorway. In one or more embodiments, the door 36 forms a portion of the x-ray shielding 30 so that the shielding fully encloses the space that receives the specimen holder 24. Thus, the door 36 may be formed from x-ray-shielding material (e.g., a steel, a lead, a metal-impregnated polymer). As shown in FIG. 3, the illustrated cabinet x-ray device 12 further comprises a pair of redundant electronic interlocks 38 configured to prevent the x-ray source 22 from operating unless the door 36 is in a closed position. That is each interlock 38 must be closed to close a circuit that provides power to the x-ray source 22. In an embodiment, the x-ray device can further comprise a solenoid-driven door lock (broadly, an automatic door lock; not-shown) configured automatically lock the door 36 in the closed position whenever the x-ray source is activated or is transmitting x-rays. This prevents the door 36 from being inadvertently opened when the x-ray source 22 is in use.

In an embodiment, the x-ray source 22 can be configured to generate an x-ray beam that is particularly suited to the task of taking x-ray images of seeds. In contrast to hard tissue such as human bone, agricultural seeds tend to have much greater x-ray transmissivity. As such, the x-ray beam produced by the source 22 can be lower energy than in conventional x-ray imaging devices. For example, in one or more embodiments, the x-ray source is configured to generate an x-ray beam having an energy of less than or equal to 40 keV. This allows a smaller x-ray source 22 to be used, which reduces weight and size in comparison with conventional cabinet x-ray devices. In the illustrated embodiment, the x-ray source 22 is configured to generate an x-ray beam in the form of a cone.

The detector 26 is configured for detecting x-rays used to form an x-ray image. In an embodiment, the x-ray detector 26 includes an onboard processor that generates an x-ray image. In certain embodiments, a controller 28 (FIG. 1; e.g., a microprocessor-based control circuit) of the x-ray device 12 is configured to generate the x-ray image based on data received from the detector 26. In one or more embodiments, the computer 14 can generate the x-ray image based on data received from the detector 26. In any case, x-ray images of the specimen can be displayed on the display 16 of the computer 14. In one or more embodiments, the computer 16 comprises a processor and a memory that stores processor-executable instructions that, when executed by the processor, function to analyze the x-ray images in accordance with one or methods of image analysis disclosed in U.S. patent application Ser. No. 16/271,005. In certain embodiments, the computer 16 can be configured to send the x-ray images to another computing device (e.g., a remote server) that analyzes the images.

Although other types of samples can be imaged using the x-ray device 12, in one or more embodiments, the holder 24 is configured to receive a sample of a plurality of seeds and position the seeds in the x-ray device for being imaged. In the illustrated embodiment, the seed holder 24 is selectively movable in the x-ray device 12 relative to the x-ray source 22 to a plurality of spaced apart predefined positions so that different portions of the seed holder can be positioned in the x-ray beam at different times. This enables imaging multiple subsets of seeds located on different portions of the seed holder 24. In an embodiment, the x-ray device 12 comprises a driver 40 that is configured to selectively move the holder 24 to a plurality of predefined positions so that the x-ray device can take discrete x-ray images of discrete subsets of seeds located on different portions of the holder.

Figure 4:
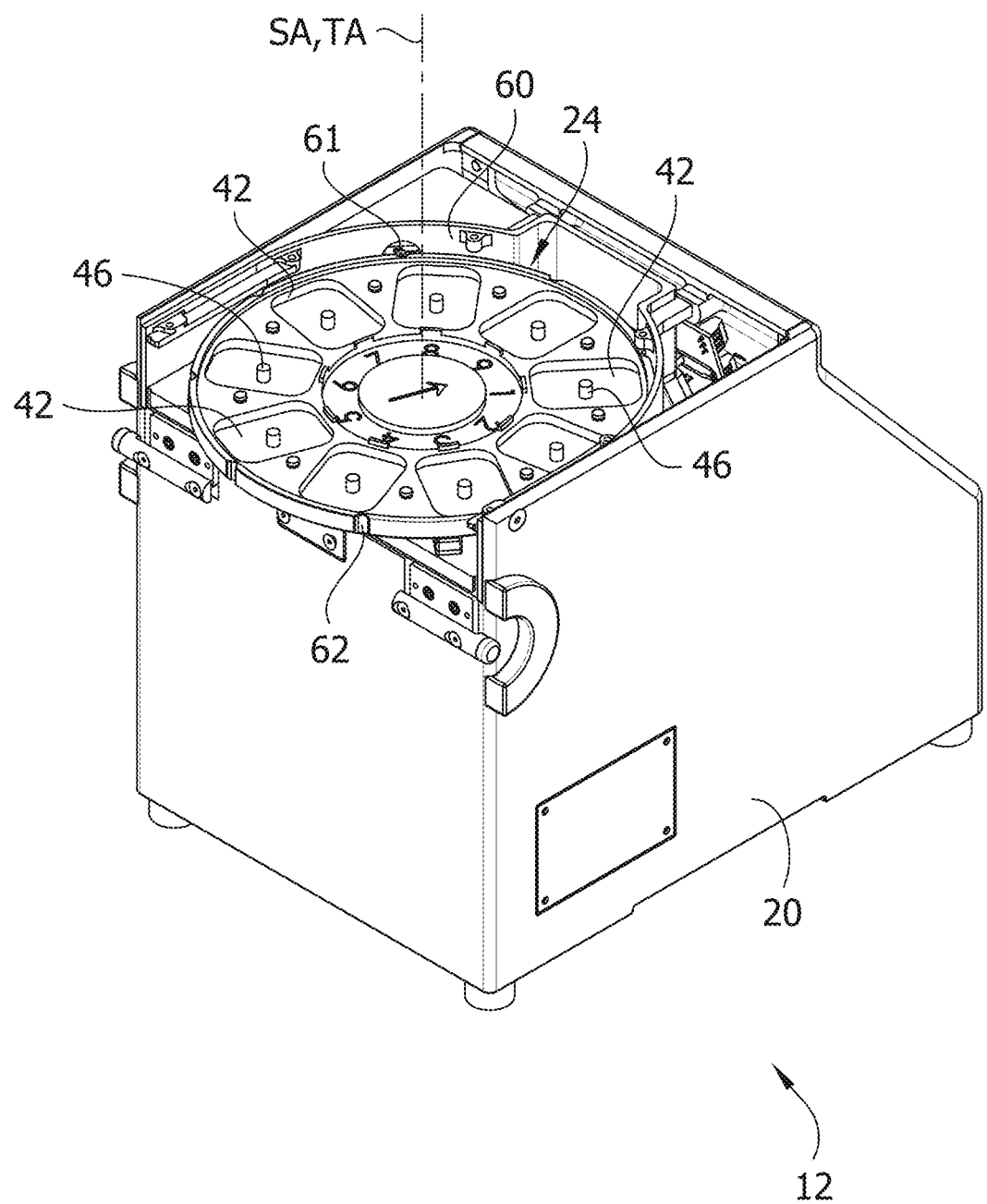
FIG. 4 is a perspective of a lower sub-assembly of the cabinet x-ray device.
Figure 5:
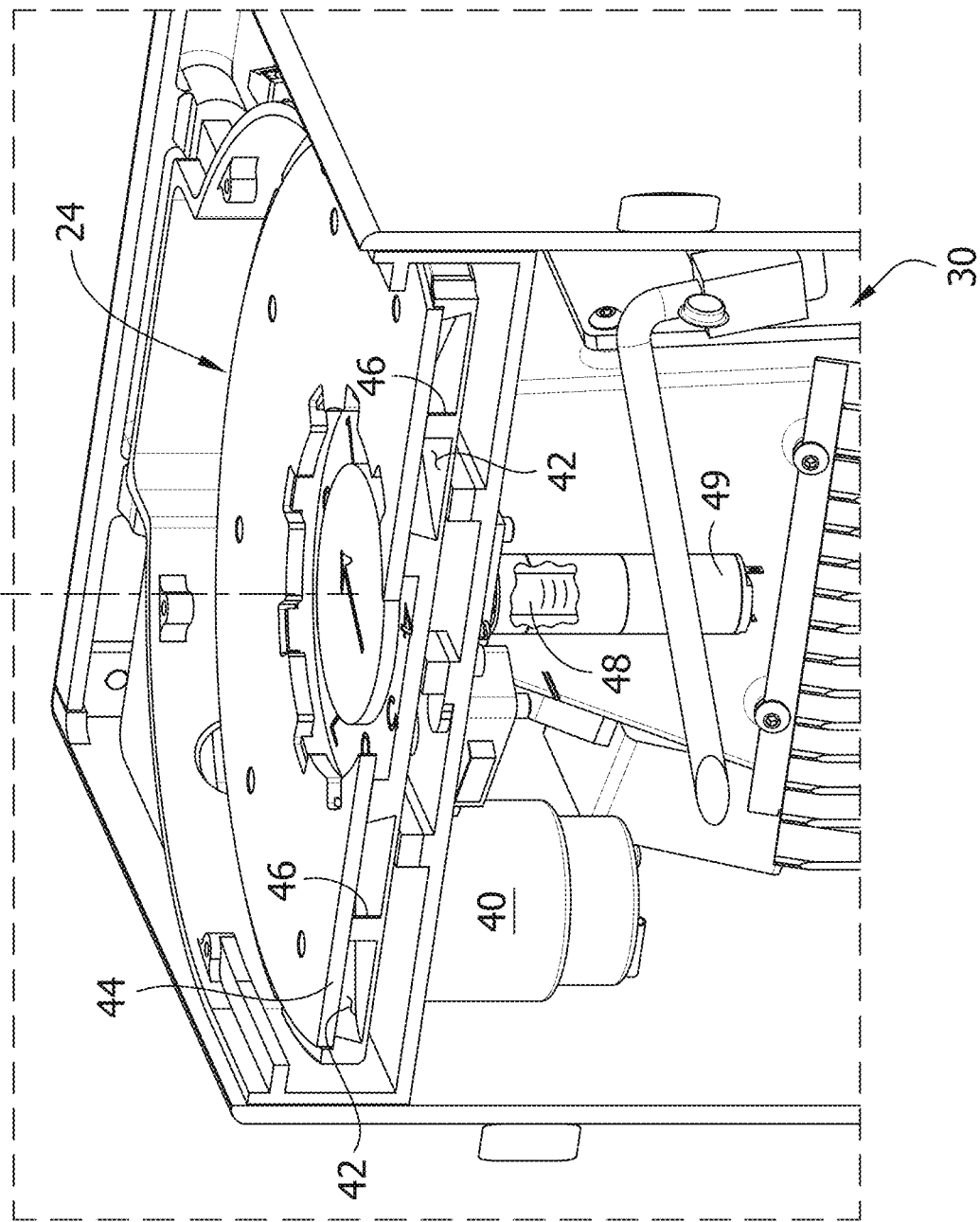
FIG. 5 is an enlarged perspective of a portion of the lower sub-assembly shown in cross-section.
Figure 6:
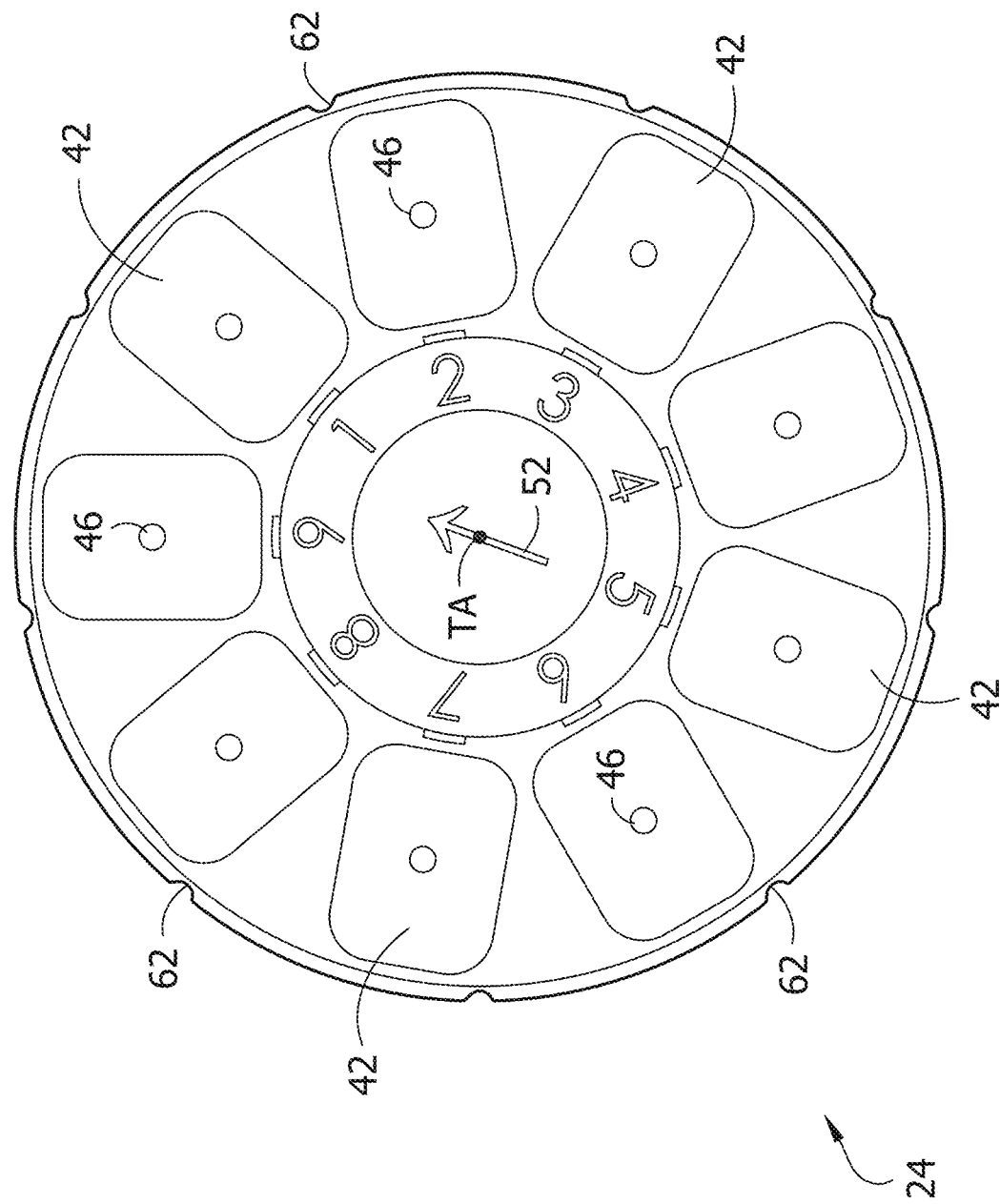
FIG. 6 is a top plan view of a seed tray of the cabinet x-ray device.

Referring to FIGS. 4-6, in one or more embodiments, the holder 24 comprises a seed tray that defines a plurality of spaced apart sample wells 42 for receiving subsets of the set of seeds in the holder. The sample wells 42 are thus configured to hold the respective subsets of seeds at spaced apart locations along the tray 24. In an embodiment, the sample wells 42 each have a depth for receiving a single layer of seeds. In one or more embodiments, a cap 44 is positioned over the tray 24 to cover the sample wells 42 and hold the single layer of seeds in position during use. The seeds may be compressed slightly between the cap 44 and the tray 24 to prevent the seeds from moving during operation. The cap 44 is transparent in the illustrated embodiment.

Suitably, all of the sample wells 42 have about the same size and shape. The size and shape of the sample wells 42 is configured so that, as the seed tray 24 moves in the x-ray device 12 to each of its predefined positions, it exposes the entirety of one, and only one, of the sample wells to the x-ray beam for x-ray imaging. In one or more embodiments, the x-ray device 12 is configured to position the tray 24 so that each sample well 42 has the same position and orientation relative to the x-ray source 22 when the tray is moved to the location at which the respective sample well is to be imaged. In other words, at each of the plurality of predefined positions of the seed tray 42, a respective one of the sample wells 42 has the same position and orientation with respect to the x-ray source 22. Thus, the x-ray images of the seeds in each sample well 42 are taken under substantially identical conditions.

In the illustrated embodiment, each sample well 42 comprises a substantially identical calibration post 46 that extends up from the bottom of the sample well 42 at about the same position. The calibration posts 46 (each, broadly, a calibration formation) should appear substantially identical in the x-ray images of each of the sample wells 42. Thus, the calibration posts 46 provide a fixed imaging reference point that can be used for calibrating the x-ray imaging device 12 or imaging software.

In the illustrated embodiment, the seed tray 24 is generally circular, and the sample wells 42 are circumferentially spaced about a center axis TA of the tray. This allows each sample well 42 to be moved into registration with the x-ray beam by sequentially rotating the seed tray 24 about its center axis TA by a predefined increment. In one or more embodiments, all of the sample wells 42 are angularly spaced apart from one another about the center axis TA of the tray by about the same amount.

Referring to FIGS. 1 and 5, the driver 40 comprises a motor that is connected to a shaft 48 to drive rotation of the shaft about a shaft axis SA. A portion of a bearing 49 of the shaft 48 is broken away in FIG. 5 to reveal the shaft. As shown in FIG. 5, in an embodiment, the motor 40 is connected to the shaft 48 by an offset drive linkage. The shaft can also be direct-driven in one or more embodiments. However, the offset drive linkage may be useful for positioning the motor so as not to interfere with the shielding 30. The seed tray 24 is configured to couple to the rotatable shaft 48 for conjoint rotation with the shaft about the shaft axis SA. For example, the seed tray 24 is configured to couple to the shaft 48 such that the center axis TA of the seed tray is generally coaxial with the shaft axis SA.

Figure 7:
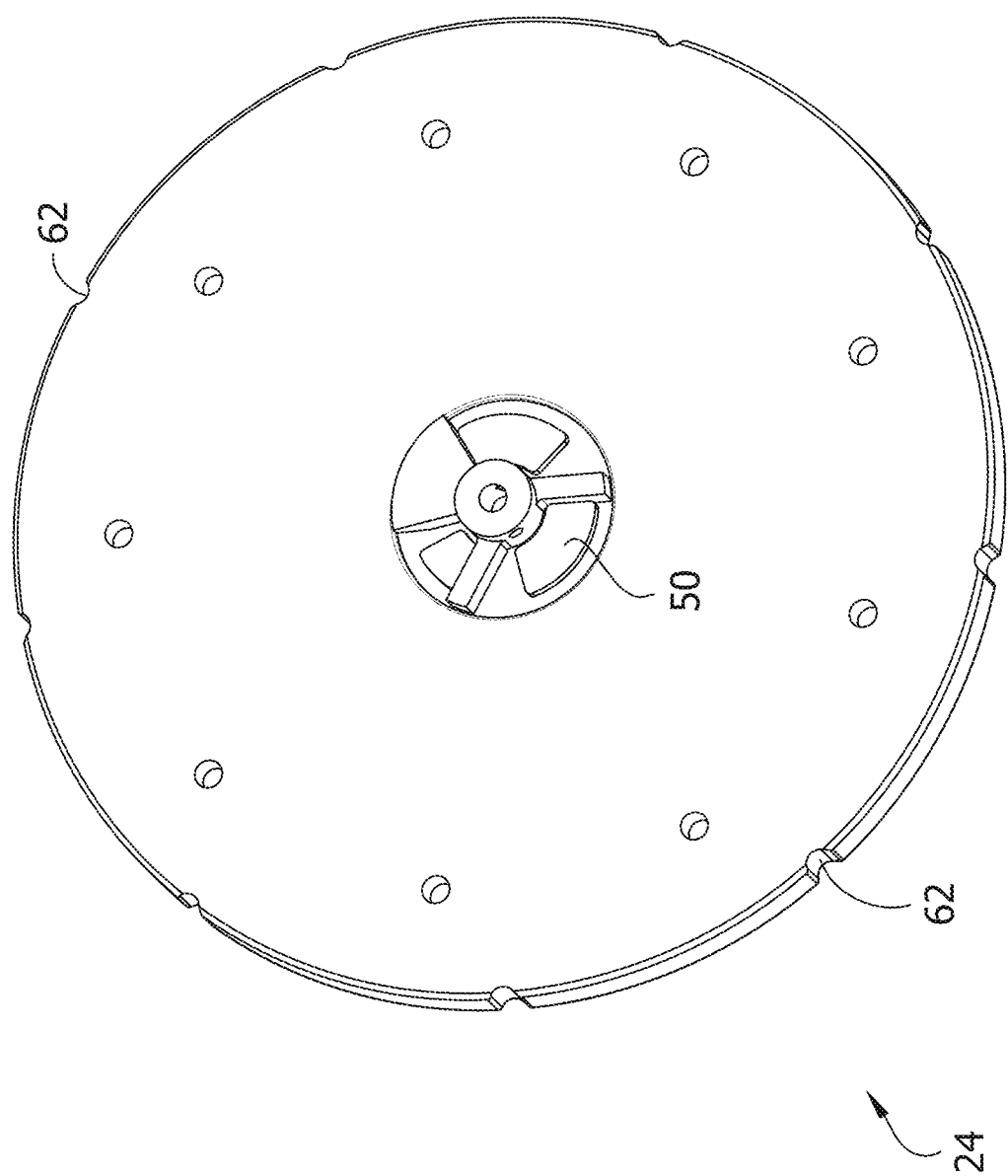
FIG. 7 is a bottom perspective of the seed tray.

Referring to FIG. 7, in one embodiment, the tray 24 comprises a key 50 configured to couple the seed holder to the shaft 48 in only one angular orientation about the shaft axis SA with respect to the shaft. This is to ensure that the sample wells 42 are imaged in a predefined sequence, e.g., a specific sample well is imaged first, second, third, and so on. As shown in FIG. 6, the illustrated tray 24 comprises an insertion arrow 52 and sequential numbering of the sample wells 42. In an embodiment, after every tray imaging operation is completed, the x-ray device 12 will automatically position the shaft 48 at the same orientation about the shaft axis SA. The arrow indicates that user should insert the tray 24 through the doorway 34 in the direction of the arrow to position the tray at the necessary orientation for the key 50 to couple the tray to the pre-positioned shaft 48.

In one or more embodiments, the controller 28 (FIG. 1) is configured to operate the motor 40 to sequentially move the seed holder 24 from the first predefined position to each subsequent predefined position until each of the sample wells 42 has been imaged. The controller 28 is further configured to hold the seed tray 24 at each of the predefined positions for at least a predefined minimum amount of time.

The predefined minimum amount of time is a sufficient amount of time for the x-ray system 10 to form an x-ray image of the seeds received in the respective sample well 42. In one or more embodiments, the predefined amount of time can be adjusted to suit the type of seeds that are being imaged. The x-ray detector 26 can run a continuous exposure during the predefined interval of time or the x-ray detector can from multiple shorter exposure images (e.g., 20 exposure images) during the predefined interval of time. In an embodiment, multiple shorter exposure images are averaged together to reduce the noise in an aggregated image of the seeds.

After imaging the seeds in any well 42, the controller is configured to activate the motor 40 and cause the motor to rotate the tray 24 toward the next predefined position. Referring to FIG. 4, in the illustrated embodiment, the x-ray device 12 comprises a switch mechanism 60 that is configured to provide a signal that the controller 28 uses to determine when to deactivate the motor 40 so that the tray 24 is then held at the next predefined position for the predefined amount of time for taking an x-ray image. In an embodiment, the switch mechanism 60 comprises a spring-loaded engagement member 61 that is configured to contact the perimeter edge of the tray 24 as the tray rotates. In some embodiments, the engagement member comprises a roller that rolls along the perimeter of the tray 24 as the tray rotates. As shown in FIG. 6, depressions 62 are formed at spaced locations along the perimeter of the tray 24. As the tray 24 rotates, the spring pushes the engagement member 61 into each depression 62 as the depression rotates into alignment with the engagement member. The locations of the depressions 62 correspond to the locations of the sample wells 42 such that, at the moment the spring moves the engagement member into a depression 61, a respective one of the sample wells becomes operatively aligned with the x-ray beam. The movement of the engagement member 61 into a depression 62 triggers an electrical switch of the switch mechanism 60, sending a signal to the controller 28 that causes the controller to deactivate the motor 40 for the predefined amount of time.

Although the illustrated x-ray device 12 uses a rotatable tray with circumferentially spaced sample wells, it will be appreciated that movable seed holders with discrete sample wells can have other configurations in other embodiments. For example, it is expressly contemplated that a seed holder can comprise grid of two-dimensional sample wells and be movable with respect to an x-ray source along two axes to position each of the sample wells in the x-ray beam for imaging. It is further contemplated that, in an embodiment, the seed holder can comprise a conveyor belt and a plurality of sample wells connected to the conveyor belt at spaced apart locations along the belt. In such an embodiment, the conveyor belt can be positioned to expose one sample well at a time to the x-ray beam as it is driven in the manner of a conventional conveyor belt. A conveyor belt of this type could be used in combination with a hopper or other automated seed loading device for loading a desired amount of seeds into the sample wells at a location upstream from the x-ray beam. In an embodiment, the conveyor belt can move continuously to present a continuous stream of seeds to the x-ray device for imaging. This type of system may involve a time delay integration in one or more embodiments. Still other movable seed holder configurations are possible within the scope of this disclosure.

Figure 8:
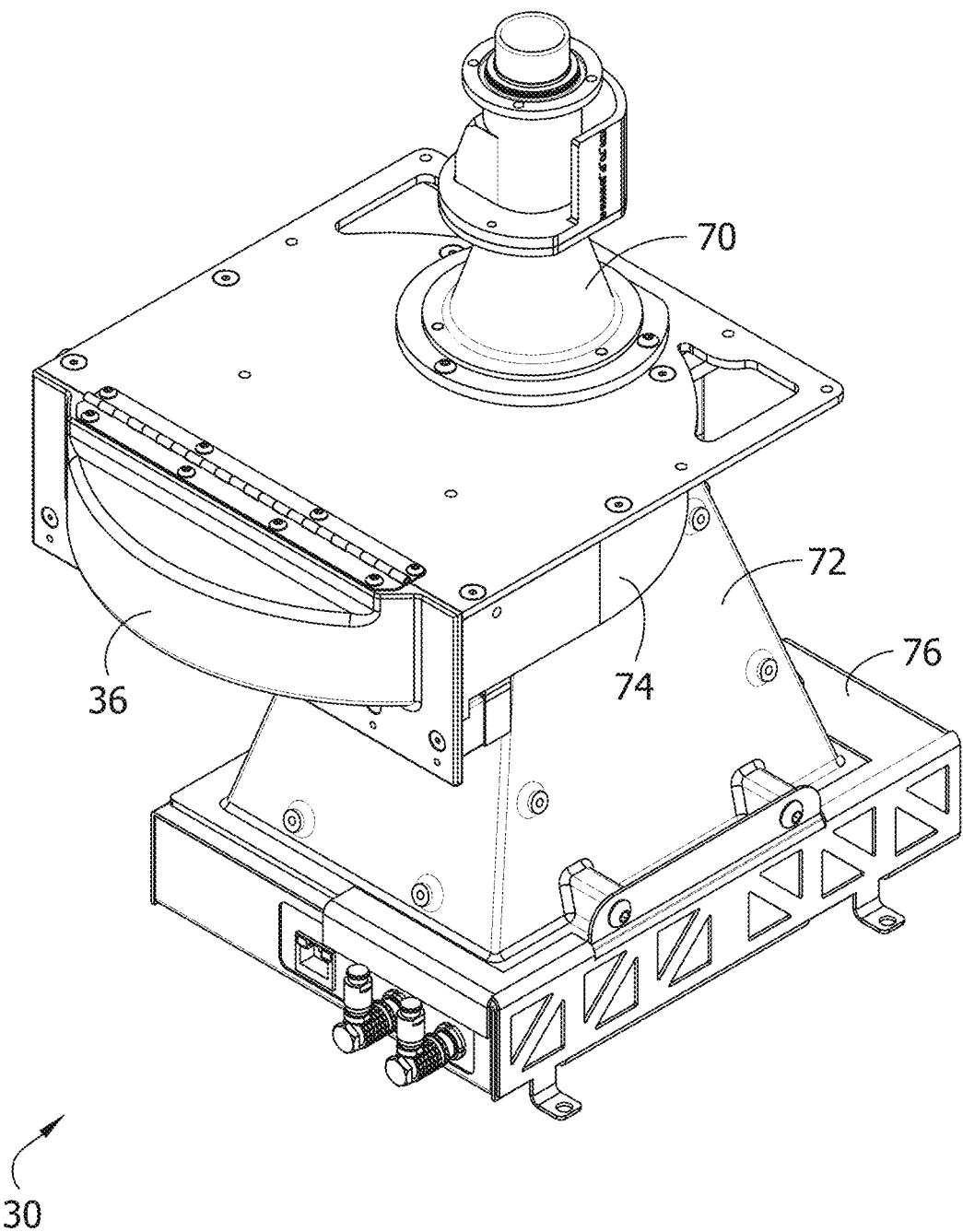
FIG. 8 is a perspective of x-ray shielding of the cabinet x-ray device.
Figure 9:
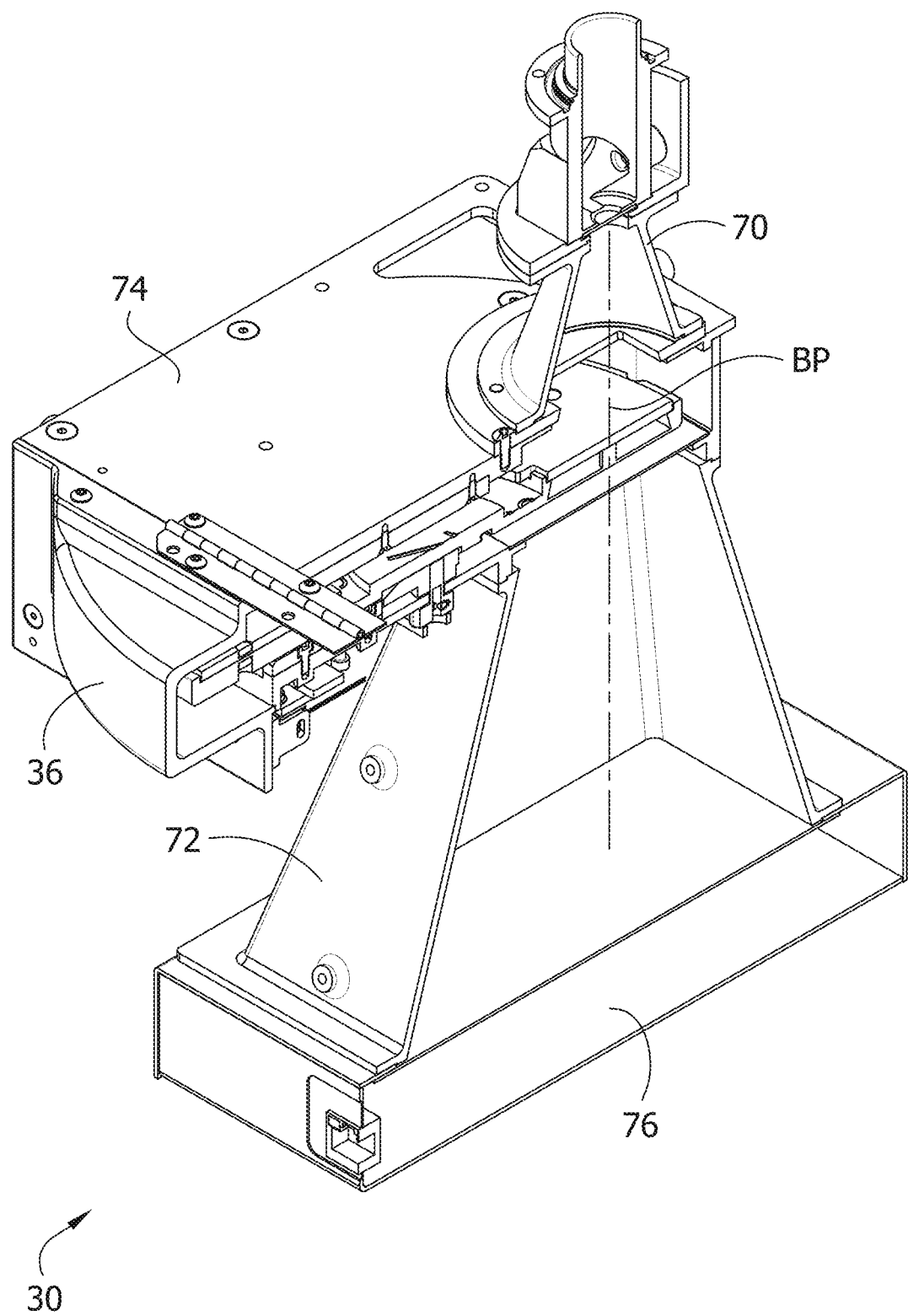
FIG. 9 is a perspective of the x-ray shielding shown in cross-section.

Referring to FIGS. 8 and 9, the x-ray shielding 30 is configured to surround the x-ray beam along the beam path BP from the x-ray source 22 to the x-ray detector 26. In the illustrated embodiment, the x-ray shielding 30 has an upstream portion 70 adjacent the x-ray source, a downstream portion 72 adjacent the x-ray detector, and a receiver portion 74 located between the upstream portion and the downstream portion. The receiver portion 74 connects the upstream portion 70 to the downstream portion 72. The receiver portion 74 is also configured to receive the seed tray 24 when the tray is positioned in the cabinet x-ray device 12. The door 36 is also coupled to the receiver portion 74. In the illustrated embodiment, the receiver portion 74 is supported on the downstream portion 72 and the upstream portion 70 is supported on the receiver portion. As a unit, the shielding 30 is self-supporting.

As explained above, the x-ray source 22 is configured to generate a cone-shaped x-ray beam. Thus, in the illustrated embodiment, the upstream and downstream portions 70, 72 have cross-sectional dimensions that increase with distance from the x-ray source 22. In other words, the cross-sectional size of the interior of the shielding 30 generally increases along the beam path BP. In the illustrated embodiment, the upstream portion 70 comprises a circular cone shape and the downstream portion 72 comprises a larger rectangular pyramid shape. In one or more embodiments, the downstream portion 72 of the shielding 30 is mounted on a detector box 76. The detector box 76 is formed from shielding material and is configured to receive the detector 26 therein. The detector box 76 thus provides shielding around the area in which the detector 26 is received.

In the illustrated embodiment, the shielding 30 is constructed to support the weight of the x-ray source 22. In an embodiment, the shielding can also or alternatively support the weight of the x-ray detector 26. In the illustrated embodiment, the x-ray source 22 is mounted directly on the upstream portion 70 of the shielding 30. To provide an adequate structure for supporting the x-ray source 22, the illustrated shielding 30 is formed from a steel such as stainless steel instead of the more conventional lead. Although lead provides more efficient shielding, it is not as strong or as machine-workable as stainless steel. The inventors have recognized that, because the x-ray energies required to image seeds are relatively low, less shielding effect is required than for conventional x-ray imagers. The inventors have further recognized that the overall weight of the x-ray device 12 can be reduced by using the shielding as the structural support for the x-ray source. Using stainless steel for the shielding 30 provides the desired amount of x-ray blocking and also provides sufficient strength and rigidity to use the shielding as the support for the x-ray source 22. In one or more embodiments the stainless steel shielding 30 is at least about 2.5 mm thick. In testing, it was found that 2.5 mm-thick stainless steel limits external x-ray exposure to less than 0.25 mR/hr when the x-ray source 22 is operated at 40 keV energy.

Although one embodiment uses stainless steel to provide self-supporting x-ray shielding 30, other materials may be used in other embodiments. For example, it is expressly contemplated that, in an embodiment, the shielding 30 is formed from a metal-impregnated polymer such as polymer impregnated with tungsten or bismuth.

Now that an embodiment of an x-ray imaging system 10 and an embodiment of a cabinet x-ray device 12 have been described, certain methods of using the x-ray device and imaging system will be described. As introduced above, the x-ray imaging system 10 is well suited for being used to analyze seeds at locations remote from a production facility at which a seed process is conducted. In an exemplary method of using the x-ray imaging system, a user loads the x-ray device 12 into a truck or other vehicle and transports the x-ray device, along with the computer 14, to the remote location (e.g., an agricultural facility where the seeds are grown or held prior to being transported to a manufacturing facility). In an embodiment, the x-ray device 12 is loaded into a robust carrying case during transport.

Once the system 10 is transported to the site, the user opens the case and inspects the x-ray device 12 for damage. Assuming no damage is found, the user removes the x-ray device 12 from the case and positions it in an upright position. The user then connects the x-ray device 12 to the computer 14 (e.g., via a USB cord) and connects the x-ray device to an available power source (e.g., an AC wall socket or vehicle battery). The user then turns the x-ray device 12 on and opens imaging software on the computer 14. After initializing the x-ray device in software, an x-ray survey is performed. In the x-ray survey, a known control is imaged to ensure proper calibration and performance of the x-ray device 12 and/or imaging software.

To image seed samples, the user loads a set seeds from the site into a tray 24. Specifically, the user loads subsets of about the same number of seeds into each sample well 42. In an embodiment, the seeds are fuzzy cotton seeds. However, other types of seeds, such as corn seeds, soybean seeds, canola seeds, wheat seeds, or vegetable seeds can also be used if desired. In an embodiment, the seeds are situated to substantially fill each sample well with a layer of seeds that is one-seed thick. When all of the wells 42 have been filled with respective seed samples, the user then secures the cap 44 to hold the seeds in the wells.

To load the seed-filled tray 24 into the x-ray device 12, the user opens the door 36 and then inserts the tray in the direction of the arrow indication 52. The key 50 couples the tray 24 to the shaft 48 for conjoint rotation with the shaft. The user then shuts the door 36 and actuates an automated seed imaging operation. Shutting the door closes the circuits to the x-ray source 22, allowing the seed imaging operation to begin.

During an automated seed imaging operation, the controller 28 automatically conducts the following sequence of operations: When the seed imaging operation is initiated, the controller 28 activates the automatic door lock (not shown) to lock the door 36 in the closed position. The controller 28 then activates the x-ray source 22 to transmit an x-ray beam. The x-ray beam passes through the seeds in the first sample well 42, and the detector 26 detects the shadow of the x-ray beam. The controller operates in this configuration for a predetermined amount of time that is sufficient to form an x-ray image of the seeds in the first well 42 based on the shadow detected by the detector 62.

After the predetermined amount of time elapses, the controller activates the motor 40. The motor rotates the shaft 48 about the shaft axis SA, thereby rotating the tray 26 about its center axis TA. As the tray 24 rotates, the engagement member 61 of the switch mechanism contacts the perimeter of the tray. When the tray 24 rotates to the predefined position for imaging the second sample well, the spring of the switch mechanism 60 pushes the engagement member 61 into the corresponding recess 62 on the perimeter of the tray. This causes the switch mechanism 60 to send a signal to the controller 28, and the controller responds to the signal by deactivating the motor 40 for a second predefined period of time. During the second predefined period of time, the x-ray source 24 transmits the x-ray beam and the x-ray beam passes through the seeds in the second well 42. The detector 26 detects the shadow of the x-ray beam passing through the second seed sample for the predetermined length of time before the controller 28 reactivates the motor 40 to rotate the tray 24 toward the third predefined position.

The controller 28 repeats this process for each of n wells 42 in the tray 24. In the illustrated embodiment, the number of wells n equals nine, but other numbers of wells could be used in other embodiments. The controller 28 suitably recognizes when the process has been repeated n times and then deactivates the x-ray source 22. In an embodiment, after deactivating the x-ray source 22, the controller 28 maintains the automatic door lock (not shown) in the locked configuration for a predetermined period of time before unlocking the door 36 so that the user can open the door and retrieve the tray 24. The user can repeat the automated seed imaging operation for additional trays 24 of seeds if desired.

The automated seed imaging operation described above has been conducted to image a tray 24 comprising nine sample wells 42 filled with fuzzy cotton seeds. A complete seed imaging operation can be conducted in under thirty minutes to form x-ray images of more than 200 fuzzy cotton seeds.

After the shadow of the x-ray beam passing through a sample of seeds is detected for the predetermined amount of time, a processor uses the data acquired by the detector 26 to form x-ray images of the seeds. In one or more embodiments, the system 10 displays the x-ray images to the user on the display 16. In an embodiment, software for analyzing x-ray images of seeds (broadly, an image analyzer) is run on the computer 14 to evaluate one or more parameters of the seeds onsite. In certain embodiments, the computer 16 transmits data representing the x-ray images to an offsite computer, which analyzes or stores the images.

Based on the displayed images and/or image analysis a user can evaluate one or more parameters of the seeds onsite. For example, the user can evaluate the quality of the seeds that were imaged. Based on the determined parameters, the user can take certain actions in regard to the seeds available at the site. For example, if the determined parameters indicate that the seeds grown or held at the site where the images were taken do not meet certain quality standards, the user can reject seeds from that site. If in contrast, the determined parameters indicate that the seeds grown or held at the site do meet required quality standards, the user can accept seeds from that site. Seeds from the site will then be transported to a remote manufacturing facility where the seeds will be further processed. Thus, it can be seen, that the portable x-ray system can be used to provide on-site evaluation of seeds so that seeds from sites can be accepted or rejected on the basis of measured quality before they are shipped to the manufacturing site.

When the desired onsite seed imaging is complete, the user can remove the seeds from the tray 24, clean the tray, turn off the computer 14 and the x-ray device 12, unplug the x-ray device from the power source 18 and the computer, clean the x-ray device, and return the x-ray device to the case. The case can then be loaded back onto the vehicle and transported to another location.

It can be seen that the seed imaging system 10 may have wide application to measuring seed parameters and/or the performance of seed processes. In another example, the seed imaging system 10 can be used to perform a method of evaluating a seed process having a plurality of process steps carried out at discrete locations. The seed imaging system 10 is transported to each of the discrete locations. At each location, seeds from the process step are collected and imaged using the techniques discussed above. Then, based on the images, the user can evaluate the effect of each process step on the seeds. For example, if a process step is causing regular damage to the seeds, the damage will appear in the x-ray images of the seeds taken from that process step. This allows the user to identify a source of seed damage and take corrective action with respect to the process.

Figure 10B:
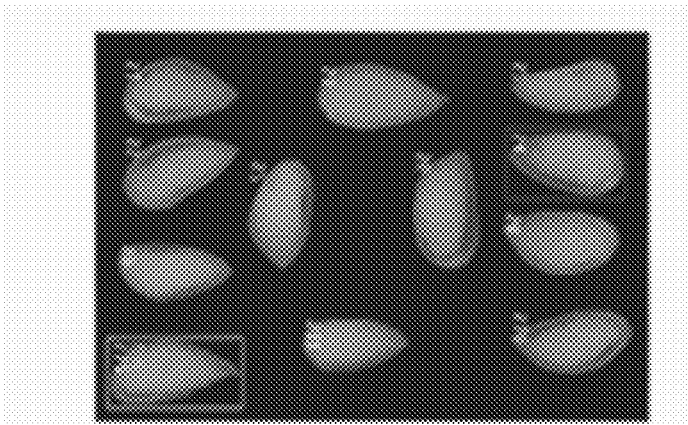
FIG. 10B is an x-ray image of a set of seeds taken by a commercial x-ray imaging device.
Figure 10A:
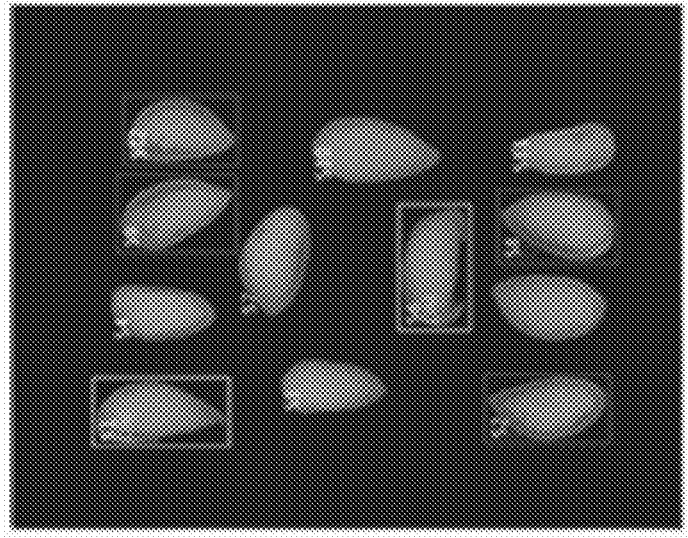
FIG. 10A is an x-ray image of a set of seeds taken by the cabinet x-ray device.

The illustrated cabinet x-ray device 12 has been manufactured and subjected to proof-of-concept testing. The shielding 30 has been found to limit external x-ray exposure to less than 0.25 mR/hr when the x-ray source is operated at 40 keV. In addition, the x-ray device 12 was operated in a climate-controlled chamber at a range of environmental conditions of from 40° F. to 100° F. and 10% relative humidity to 80% relative humidity. The device 12 was found to produce x-ray seed images of the desired quality at the full range of tested environmental conditions. In regard to image quality, x-ray images of a set of seeds were taken on the x-ray device 12 and a commercial-grade Faxitron x-ray imager, used to provide a benchmark. The x-ray images from the two devices are shown in FIGS. 10A and 10B. As can be seen, there is very little difference in image quality or appearance. Further, the performance of the x-ray device 12 at resolving line pairs was tested directly, and it was found that the x-ray device could resolve line pairs of greater than 20 line pairs-per-mm.

As can be seen, the illustrated seed imaging system 10 can be used to image or analyze seeds at nearly any location where seeds can be found.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A cabinet x-ray device for imaging seeds, the cabinet x-ray device comprising:
   an x-ray source configured to transmit an x-ray beam along a beam path;
   a seed holder configured to receive a plurality of seeds and be selectively positioned in the cabinet x-ray device such that the beam path crosses the seed holder and the x-ray beam passes through at least some of the seeds received in the seed holder, the seed holder including a plurality of sample wells at spaced apart locations, each of the sample wells configured to receive a set of the plurality of seeds; and
   an x-ray detector configured to detect the x-ray beam after passing through the seeds such that one or more x-ray images of the seeds can be formed based on the detected x-ray beam.

2. The cabinet x-ray device as set forth in claim 1, wherein the seed holder is movable relative to the x-ray source to a plurality of spaced apart predefined positions, wherein at each of the predefined positions, the beam path crosses a respective one of the plurality of sample wells such that the x-ray beam passes through the respective at least one of the plurality of seeds received in the sample well.

3. The cabinet x-ray device as set forth in claim 2, wherein at each of the predefined positions of the seed holder, the x-ray beam intersects only one of the sample wells.

4. The cabinet x-ray device as set forth in claim 2, further comprising a driver configured to drive movement of the seed holder to each of the predefined positions.

5. The cabinet x-ray device as set forth in claim 4, further comprising a controller configured to operate the driver to sequentially move the seed holder to each of the predefined positions and to hold the seed holder at each of the predefined positions for at least a predefined minimum amount of time.

6. The cabinet x-ray device as set forth in claim 5, wherein the driver comprises a motor connected to a shaft to drive rotation of the shaft about a shaft axis, the seed holder configured to couple to the rotatable shaft for conjoint rotation with the shaft about the shaft axis.

7. The cabinet x-ray device as set forth in claim 6, wherein the seed holder comprises a key configured to couple the seed holder to the shaft in only one angular orientation about the shaft axis with respect to the shaft.

8. The cabinet x-ray device as set forth in claim 7, wherein the sample wells are angularly spaced apart about the shaft axis when the seed holder is coupled to the shaft.

9. The cabinet x-ray device as set forth in claim 6, wherein the plurality of predefined positions of the seed holder are angularly spaced apart about the shaft axis.

10. The cabinet x-ray device as set forth in claim 2, wherein the seed holder comprises a generally circular tray having a center axis, the sample wells being angularly spaced apart about the center axis of the tray.

11. The cabinet x-ray device as set forth in claim 1, further comprising a cabinet having a doorway and a door movable relative to the cabinet to open and close the doorway, the seed holder being selectively passable through the doorway when the doorway is open.

12. The cabinet x-ray device as set forth in claim 11, further comprising a locking mechanism configured to automatically lock the door in a position at which the door closes the doorway when the x-ray source is transmitting x-rays.

13. The cabinet x-ray device as set forth in claim 1, further comprising x-ray shielding configured to extend circumferentially around the x-ray beam along the beam path from the x-ray source to the x-ray detector.

14. The cabinet x-ray device as set forth in claim 13, wherein the x-ray source has a weight and the x-ray shielding supports the weight of the x-ray source.

15. The cabinet x-ray device as set forth in claim 13, wherein the x-ray shielding is made of one of a steel and a metal-impregnated polymer.

16. The cabinet x-ray device as set forth in claim 11, wherein the cabinet x-ray device has a total weight of less than 50 pounds.

17. The cabinet x-ray device as set forth in claim 1, wherein the x-ray source is configured so that the x-ray beam has an energy of less than or equal to 40 keV.

18. A cabinet x-ray device, the cabinet x-ray device comprising:
an x-ray source configured to transmit an x-ray beam along a beam path, the x-ray source having a weight;
a seed holder configured to receive a plurality of seeds and be positioned in the cabinet x-ray device such that the beam path crosses the seed holder and the x-ray beam passes through at least some of the seeds received in the seed holder;
an x-ray detector configured to detect the x-ray beam, the x-ray detector having a weight; and
x-ray shielding that extends circumferentially around the beam path from the x-ray source to the x-ray detector, the x-ray shielding including (i) an upstream portion disposed adjacent the x-ray source and generally above the seed holder when the seed holder is positioned in the cabinet x-ray device and (ii) a downstream portion disposed adjacent the x-ray detector and generally below the seed holder when the seed holder is positioned in the cabinet x-ray device, wherein the upstream portion of the x-ray shielding is separate from the downstream portion of the x-ray shielding, and wherein the x-ray shielding is configured to limit transmission of x-rays from the x-ray beam outside of the x-ray shielding;
wherein the x-ray source is mounted on top of the upstream portion of the x-ray shielding such that the weight of the x-ray source is supported on the x-ray shielding.

19. The cabinet x-ray device as set forth in claim 18, wherein the x-ray shielding includes a receiver portion located between the upstream portion and the downstream portion, and wherein the receiver portion is configured to receive the seed holder in the cabinet x-ray device.

20. The cabinet x-ray device as set forth in claim 18, wherein the upstream portion and the downstream portion have cross-sectional dimensions that increase with distance from the x-ray source.

21. A method of evaluating seeds, the method comprising:
placing a set of seeds into each of a plurality of sample wells in a seed holder;
positioning the seed holder in a cabinet x-ray device at a plurality of spaced apart predefined positions, wherein an x-ray beam of the cabinet x-ray device intersects each of the sample wells at a respective one of the plurality of predefined positions of the seed holder; and
taking an x-ray image of a respective set of seeds using the cabinet x-ray device when the seed holder is positioned at each of the predefined positions.

* * * * *